United States Patent [19]
Buchner et al.

[11] 4,258,575
[45] Mar. 31, 1981

[54] ULTRASONIC IMAGING APPARATUS OPERATING ACCORDING TO THE IMPULSE-ECHO METHOD

[75] Inventors: Klaus Buchner, Uttenreuth; Rainer Haerten, Erlangen, both of Fed. Rep. of Germany

[73] Assignee: Siemens Aktiengesellschaft, Berlin & Munich, Fed. Rep. of Germany

[21] Appl. No.: 15,740

[22] Filed: Feb. 27, 1979

[30] Foreign Application Priority Data

May 11, 1978 [DE] Fed. Rep. of Germany ....... 2820660

[51] Int. Cl.³ ............................................. G01N 29/04
[52] U.S. Cl. .......................................... 73/626; 73/628
[58] Field of Search .................. 73/626, 628; 128/660; 367/11; 358/112

[56] References Cited

U.S. PATENT DOCUMENTS

| | | | |
|---|---|---|---|
| 4,010,466 | 3/1977 | Hofstein | 367/11 |
| 4,135,139 | 1/1979 | Buchner | 73/626 |
| 4,135,140 | 1/1979 | Buchner | 73/626 |
| 4,174,705 | 11/1979 | Buchner | 73/626 |

FOREIGN PATENT DOCUMENTS

2619684 11/1976 Fed. Rep. of Germany .

*Primary Examiner*—Anthony V. Ciarlante
*Attorney, Agent, or Firm*—Hill, Van Santen, Steadman, Chiara & Simpson

[57] ABSTRACT

An exemplary embodiment comprises an ultrasonic applicator for line-by-line ultrasonic scanning and a picture tube, for example, a television monitor for the visible echo image. The echo lines developing from the ultrasonic applicator are alternately stored in alternating memories and read out to the picture tube. The reading-out ensues singly or multiply in such reading-out times as correspond to the line sweep time of the picture tube. An imaging apparatus is desired which, in addition to direct reproduction, also renders possible the reproduction of stored ultrasonic images given the smallest technical outlay while doing without extravagant image memories. This is achieved in that, in addition to the alternating memories, at least one echo line auxiliary memory is present which is connectable to the signal path between the ultrasonic applicator and the alternating memories for rolling-in current echo lines of an ultrasonic image and for later reading-out of stored lines via the alternating memories to the picture tube. The invention is employed, above all, in ultrasonic tomographic diagnostics.

9 Claims, 2 Drawing Figures

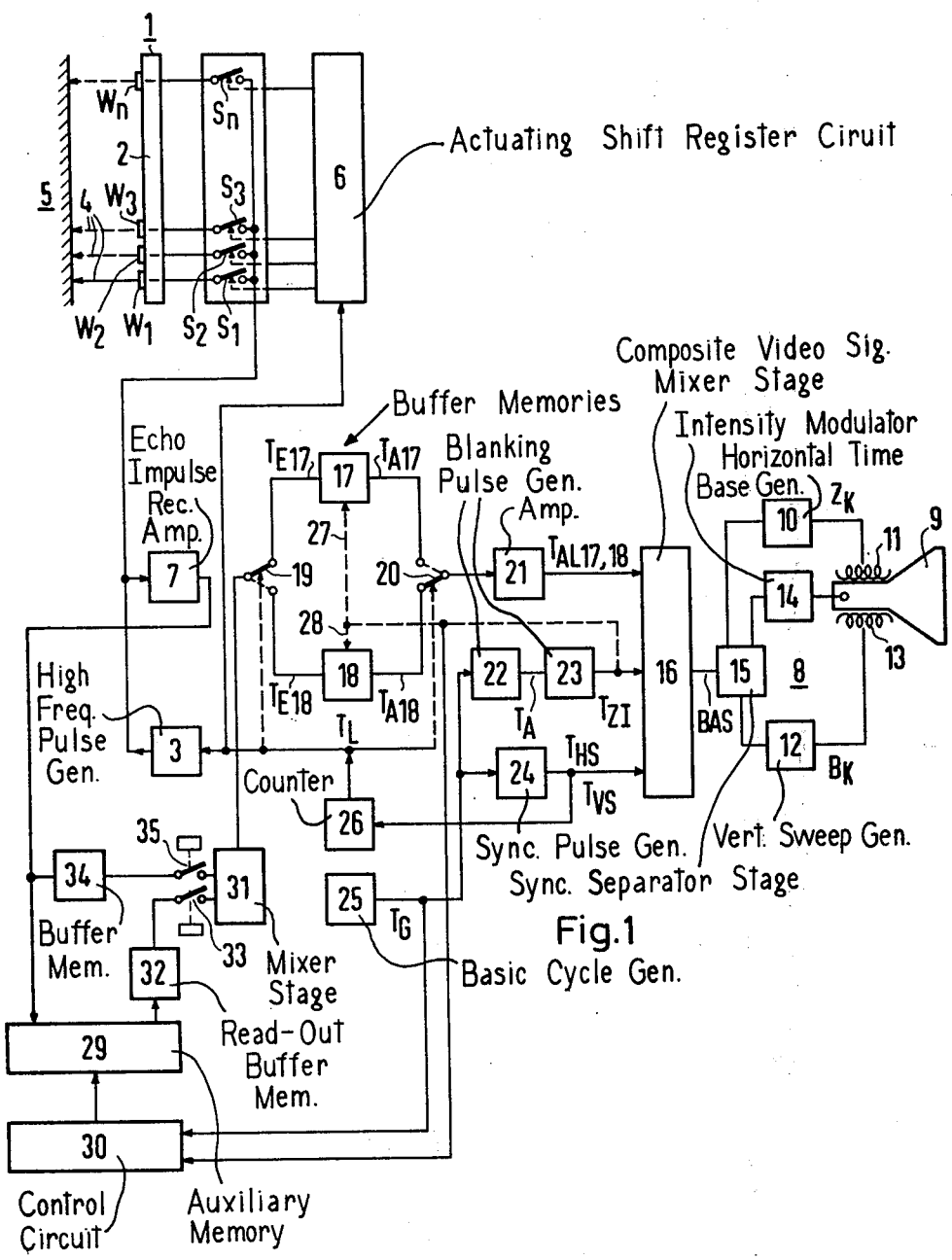

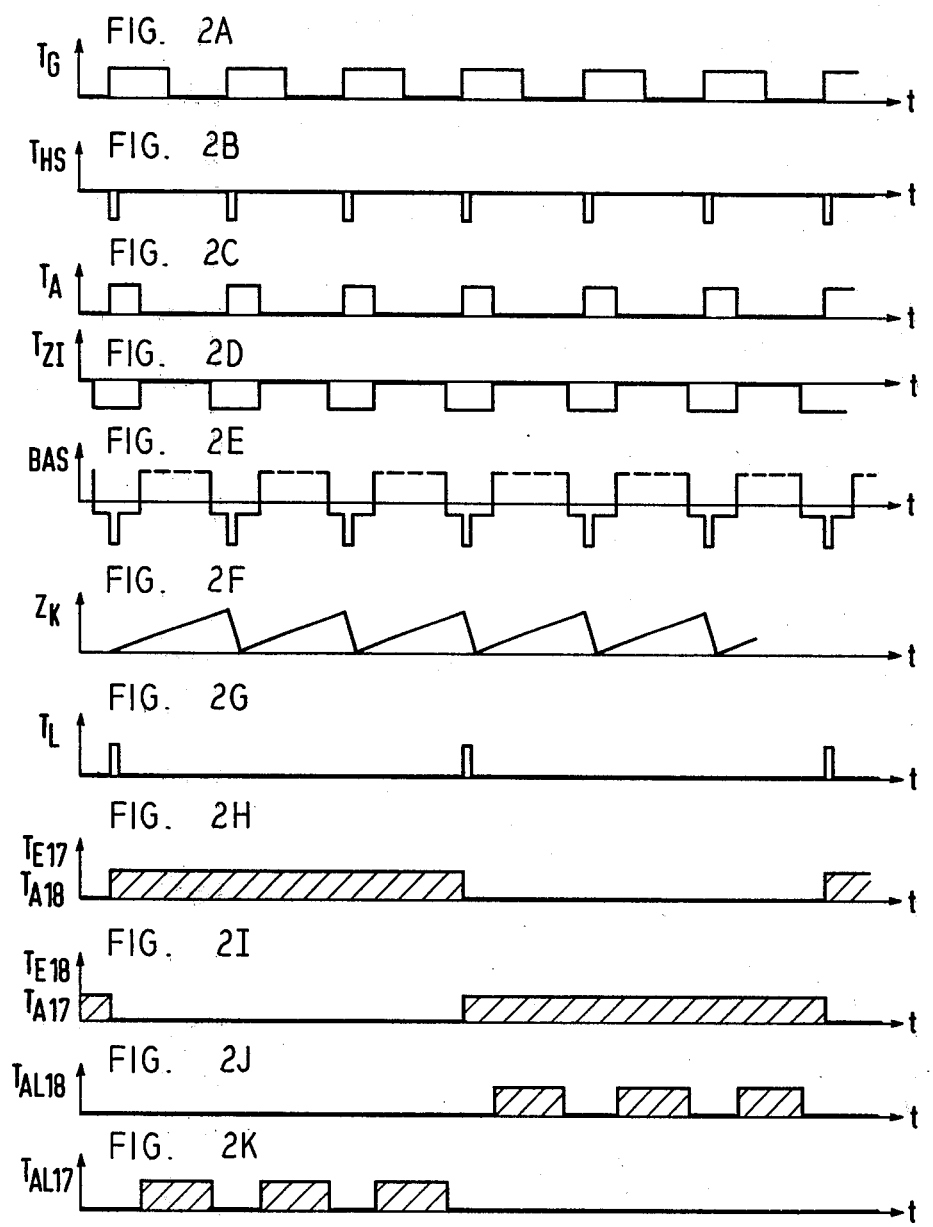

ULTRASONIC IMAGING APPARATUS OPERATING ACCORDING TO THE IMPULSE-ECHO METHOD

BACKGROUND OF THE INVENTION

The invention relates to an ultrasonic imaging apparatus operating according to the impulse-echo method, particularly intended for medical diagnostics, comprising an ultrasonic applicator for the linear ultrasonic scanning of an examination subject and an image display device with a line generator for the reproduction of the echo impulses as lines, as well as an image generator for the displacement of the line as a function of the displacement of the ultrasonic beam in the subject, whereby, proceeding from a prescribable line sweep time of a picture tube as the image display installation, for example, from the standard line sweep time of a television picture tube, the period time of the ultrasonic transmission/reception cycles of the ultrasonic applicator is adjusted to a value which corresponds to a whole multiple of the line sweep time of the picture tube and whereby echo signals arising at the rate of these transmission/reception cycles are stored for each cycle in alternating memories until the next successive one and are only read out to the picture tube during this next succesive cycle, whereby the reading out ensues singly or mutliply in such reading-out times which correspond to the line sweep time of the picture tube.

Such an imaging apparatus is known for example from the German Offenlegungsschrift No. 2,629,895. It specifically renders possible a video-standard conversion with only a maxiumum of two memories for the intermediate storage of the echo signals of two respective successive scanning lines. Thereby, the conversion of the ultrasonic image ensues in the direct process.

In practice, not only the direct presentation of the image directly scanned at the current point in time is of interest; the reproduction of stored images is also of significance. By this means, one obtains a stationary image which facilitates the mensuration of the ultrasonic image on the picture screen. The diagnostic statement is also facilitated by means of stationary images, for example, upon later reproduction.

For the presentation of digitally stored images, particularly in the television standard, up to now total image memories (so-called orthogonal memories) which have a very high technical outlay were required, with whose help, thus, only an already converted, complete image could be stored and again polled. An ultrasonic image apparatus with such a memory system is already known, for example, from the German Offenlegungsschrift No. 2,619,684.

SUMMARY OF THE INVENTION

The object of the present invention is to create an imaging arrangement for the conversion of ultrasonic images into a prescribable image type, for example, in television standard, which, in addition to direct reproduction, also renders the reproduction of stored ultrasonic images possible with the smallest technical outlay. The reproduction of stored images should also preferably be able to ensure simultaneously with a current image.

The object is achieved with an ultrasonic imaging apparatus of the type initially cited in that, in addition to the alternating memories, at least one echo-line auxiliary memory is present which can be connected to the picture tube at the signal path between the ultrasonic applicator and the alternating memories via the alternating memories for reading in current echo lines of a ultrasonic image and for the later re-reading-out of stored lines.

Solely by the use of an echo-line auxiliary memory which requires little technical outlay in place of an extravagant and expensive total image memory, the invention renders possible the image recording of previously stored ultrasonic echo images in the reproduction manner desired. The recording of the stored images can ensue independently of the presentation of current images; as needed, however, the recording of stored images together with the presentation of a current image is just as easily possible.

Further advantages and details of the invention follow from the detailed description of an exemplary embodiment on the basis of the accompanying sheets of drawings in conjunction with the subclaims; and other objects, features and advantages will be apparent from this detailed disclosure and from the appended claims.

BRIEF DESCRIPTION OF THE DRAWINGS

FIG. 1, in a basic circuit diagram, shows an ultrasonic imaging apparatus according to the invention specifically for conversion into a television standard display; and FIG. 2 shows a pulse diagram for explaining the implementation of a video-standard conversion according to the invention with the basic circuit diagram according to FIG. 1.

DETAILED DESCRIPTION

In FIG. 1, 1 designates the ultrasonic applicator which, in the present instance, is constructed in the form of an ultrasonic array. Accordingly, applicator 1 consists of a plurality of ultrasonic transducers $W_1$ through $W_n$ (piezo-electric crystal lamellae), which are supported adjacently of one another in a row on a carrier section 2 consisting of a material having good ultrasonic wave-attenuating properties. The individual transducer elements $W_1$ through $W_n$ are capable of being selectively energized individually or in groups by high frequency impulses of a high frequency pulse generator 3 in such a manner that they radiate ultrasonic impulses in the direction of arrows 4 into an examination subject 5, e.g. a human body. The actuation of the individual transducer elements $W_1$ through $W_n$ individual or group formation proceeds by means of an actuating mechanism comprising, in the conventional manner, an actuating shift register 6 as well as actuating switches $S_1$ through $S_n$ for the purpose of connecting transducer elements which are to be energized to high frequency impulse generator 3 in the transmit mode, or connecting them to an echo impulse receiving amplifier 7 in the receive mode. The actuating mechanism operates with shift register 6 in such a manner that the individual transducer elements $W_1$ through $W_n$ can be switched to transmit or receive in continuous succession across the transducer row individually or in groups by means of correspondingly actuated switches $S_1$ through $S_n$. In this manner, there is a resulting linear progression of the ultrasonic transmitting/receiving beam across the transducer row and a consequent corresponding linear ultrasonic scanning of the examination subject 5. A traditional (conventional) television monitor 8 serves for recording the echo signals of each ultrasonic scanning line as a corresponding image line. This television monitor comprises a television picture tube 9, to which a horizontal time-base generator 10 for a horizontal deflection coil 11 as well as a vertical sweep generator 12 for the vertical deflection coil 13 of the television picture tube 9 is allocated in the standard manner. The monitor 8 further comprises an intensity modulator 14 for intensity modulation of the image lines of the line scanning pattern in step with the occurring echo pulses as well as a synchronizing separator stage 15 for separating the different information contents of the composite video signal (BAS, FIG. 2E) supplied to the monitor 8.

The composite video signal develops at the output of a mixer stage 16, which is fed on its input side by the echo signal information, the horizontal (and vertical) blanking pulses as well as the line (and image) synchronizing pulses. Specifically in direct scanning operation, the echo signal information is conducted from the output of the echo signal reception amplifier 7 via a series connection consisting of a buffer memory 34 with switch 35 and mixer stage 31, to be explained later, to buffer memories 17 or, respectively, 18, which function in push-pull action by means of alternating switches 19 and 20 and are supplied from there, finally, to the composite video signal mixer stage 16 via a further amplifier 21 for the echo signals. A blanking pulse generator 22, 23 and respectively, a synchronizing pulse generator 24, serve for the generation of the horizontal (and vertical) blanking pulses and, respectively, of the line (and image) synchronizing pulses. The blanking pulse generator comprises two monostable flip-flops 22 and 23 which are triggered in temporal succession at the clock rate of clock pulses $T_G$ of a basic cycle generator 25. The two pulse series $T_A$ or, respectively, $T_{ZI}$ according to FIG. 2 thus follow from the basic cycle of the basic cycle generator 25, which operates at the standardized line sweep frequency of the television picture tube 9 (of, for example, 15.625 kHz). Further, the basic cycle generator 25 also drives the synchronizing pulse generator 24 with clock pulses. The synchronizing pulse generator 24 is likewise designed as a monostable flip-flop which emits brief pulses according to the clock pulse waveform ($T_{HS}$, FIG. 2B). The composite video signal (BAS signal) then results with a temporal waveform according to FIG. 2E which shows the superposition of the respective blanking pulses (e.g. FIG. 2D) with the synchronizing pulses (e.g. FIG. 2B) and the echo information. After separation in the synchronizing separator stage 15 of the television monitor 8, the line scanning voltage ($Z_K$, FIG. 2F) is the respectively triggered by means of the horizontal synchronizing pulses. On the other hand, at the end of each image buildup, the image synchronizing pulse is generated in conjunction with an image blanking pulse which effects the return of the electron beam of the television picture tube 9 into the initial position and the retriggering of a further image sweep in conjunction with a further line scanning pattern sweep. On the other hand, a counter 26 into which the synchronizing pulses of the synchronizing pulse generator 24 are counted serves for setting the trasmission/reception times of the ultrasonic transmission/reception cycles.

In accord with the present exemplary embodiment, the counter 26 generates an output pulse $T_L$, FIG. 2G, with each fourth developing synchronizing pulse, which output pulse on the one hand serves as a control clock pulse for effecting the forward shifting in the active register positions of the shift register 6 and, thus, the periodic sequencing of the switches $S_1$ through $S_n$. On the other hand, with each occurrence of a control clerk pulse $T_L$, the high frequency pulse transmitter 3 is at the same time activated to emit a high frequency pulse to the respective transducer element $W_1$ through $W_n$ connected by means of a switch $S_1$ through $S_n$. Thus, a line-by-line ultrasonic scanning of the examination object 5 is produced at the clock rate of the control clock pulses $T_L$. Further, alternating changeover of the switches 19 and 20, also ensues via the control clock pulses $T_L$. Thereby, the changeover times at the memory inputs and, respectively, the changeover times at the memory outputs are respectively designated in FIG. 2 with $T_{E17}$ and $T_{E18}$, and $T_{A17}$ and $T_{A18}$. The pulses illustrated with shading respectively designate the duration of the feeding of echo signal information into the one memory upon simultaneous read-out of the information of a preceding echo line from the other memory. The actual read-out of the information from the memory 17 or 18 respectively connected on the output side via the amplifier 21 to the mixer stage 16 ensues, on the other hand, at the synchronizing rate of the output pulses of the blanking pulse generator 22, 23 via the read-out control lines 27, 28. Since, for the duration of the selection of a memory 17 or, respectively, 18, by means of the output switch 20, a total of three blanking pulses of the blanking pulse generator 22, 23 always respectively develop in temporal succession, accordingly, an echo line rolled into the respectively connected memory 17 or 18 is read out a total of three times in temporal succession. Thus, an echo image with high line density and relatively high image frequency results on the picture screen of the television picture tube 9, whereby, however, each line is written three times.

As described, the operation up to now ensues only in the direct scanning process, i.e. such echo lines which develop directly at the examination object in the scanning operation are, correspondingly, directly (contemporaneously) converted into the video standard and illustrated on the television monitor as a direct image.

According to the present invention, however, there is also the possibility of reproducing and displaying stored images; the stored image can then serve as the actual television picture either alone or, as a variation, the stored image (or a plurality of stored images) can also represent the television picture in superposition together with a direct (contemporaneous) image now again developing in direct scanning operation.

Accordingly, in order to implement such processes, an auxiliary memory 29 (for example, a RAM memory) for the developing echo lines of an echo image is connected at the output of the echo pulse reception amplifier 7 in the basic circuit diagram of FIG. 1. The control of the auxiliary memory for reading-in or, respectively, again reading-out lines or entire images ensues by means of a control circuit 30 as a function of the basic cycle pulses $T_G$ of the basic cycle generator 25 on the one hand and of the control pulses of the read-in or, respectively, read-out line 27, 28 for the buffer memory 17 or, respectively, 18, on the other hand. The read-out of stored lines from the auxiliary memory 29 to the alternately operating buffer memory 17 or, respectively, 18, ensues via a mixer stage 31 upon interpolation of a read-out buffer memory 32 with connection switch 33. As already initially described, the output signal of the echo pulse reception amplifier 7 is also supplied to the mixer stage 31 at a second input, again via a buffer memory 34 with switch 35, during line or image transmission in direct operation.

Thereby, the following mode of operation occurs:

Whereas with switch 35 closed, a television picture is generated in the direct process by the echo impulse reception amplifier 7 via the buffer memory 34 and the mixer stage 31, at the same time the current echo signals are written in succession line-by-line into the auxiliary memory 29 at the rate of control signals of the control circuit 30. The writing-in frequency in the auxiliary memory 29 exactly corresponds to the writing-in frequency of the corresponding lines in the buffer memory 17 or, respectively, 18. The capacity of the auxiliary memory 29 is limited to the number of the echo lines of at least one ultrasonic image multiplied by the scanning points of each line and (with digital storage of the amplitude of the echo signal at each scanning point) the number of bit positions used to encode each echo signal amplitude, i.e. the bit word length or bit depth. Depending on the position of switches 33 and 35, the mixer 31 then alternately receives in read-out operation echo signals either only from the echo impulse reception amplifier 7 via the buffer memory 34 or only from the auxiliary memory 29 via the read-out buffer memory 32 or from both at the same time. The television standard conversion, now as before, proceeds in all possible modes of operation via the alternating buffer memories 17, 18 in the mixer stage 16.

When the read-out frequency of the auxiliary memory 29 is the same as its write-in frequency, then the scale of the stored image corresponds to that which was registered in the direct scanning operation. With deviations of the read-out frequency to higher or lower values, a corresponding reduction or magnification of the scale ensues. Thus, for example, a stored, reduced total image, partial image or something similar or, respectively, such an image with magnification of a section can be mixed with the direct image (real time image). From a diagnostic standpoint, thus, any desired comparative measurements can be conducted on the basis of the direct image and the superimposed, stored partial image which, for example, is also altered in scale.

The parallel operation of the auxiliary memory 29 and the line alternating buffer memory 17 and 18 allows a simple line-wise organization of the auxiliary memory in the write and read mode and, thus, a simple addressing of the successive image points of each line.

The exemplary embodiments described works in the simple total image method. Of course, however, an interlaced scanning procedure can also be employed to the end that, with even-numbered multiples of the horizontal synchronizing pulses, ultrasonic scanning in the examination object and line image recording with the television picture tube occurs in, for example, two successive half-images, whereby the multiple writing of an echo line amounts to half of the even-numbered multiple of the horizontal sync.

It will be apparent that many modifications and variations may be effected without departing from the scope of the novel concepts and teachings of the present invention.

We claim as our invention:

1. Ultrasonic imaging apparatus operating according to the impulse-echo method, particularly for medical diagnostics, said apparatus comprising (a) an ultrasonic applicator operable for line-by-line ultrasonic scanning of an examination subject, (b) an image display device for coupling with said ultrasonic applicator, and having a line generator operable for controlling said image display device for imaging echo impulses from the ultrasonic applicator as lines, and an image generator operable for controlling said image display device for the displacement of the lines as a function of the displacement of the ultrasonic scanning in the subject, said image display device having a prescribed line scan time for real time display of a currently scanned image, (c) said ultrasonic applicator having a time period of its ultrasonic transmission/reception cycles set to a value which corresponds to an integral multiple of the prescribed line scan time of the image display device, and (d) control means operating at a clock rate and controlling the time period of said ultrasonic transmission/reception cycles, (e) sequentially operating frequency converter memories controlled by said control means for storing an input line signal corresponding to a line sequence of echo impulses to be displayed as one line on said image display device and for reading out the stored line signal at a predetermined read-out time occurring at a fixed time in relation to the operation of said image display device and at a higher frequency than that corresponding to the time period of said ultrasonic transmission/reception cycles such that the ultrasonic image currently being supplied by said ultrasonic applicator is displayed in real time, and (f) further memory, characterized in that the further memory comprises an echo line auxiliary memory (29) operable under the control of said control means for storing an input line signal from said ultrasonic applicator corresponding to a line sequence of echo impulses to be displayed as one line on said image display device, (g) signal path means connected between said ultrasonic applicator and said sequentially operating frequency converter memories and comprising a real time signal path for a current line sequence of echo impulses as supplied by said ultrasonic applicator, (h) said echo line auxiliary memory (29) being connected between said ultrasonic applicator and said sequentially operating frequency converter memories in parallel with said real time signal path, said echo line auxiliary memory being selectively operable to store a current line sequence of echo impulses under the control of said control means and being selectively operable for supplying a previously stored line sequence to said sequentially operating frequency converter memories without change of the predetermined read-out time of the stored line signals from said frequency converter memories, whereby the line sequences selectively stored by said auxiliary memory are stored and read-out in step with the time period of the ultrasonic transmission/reception cycles and at an integral multiple of the prescribed line scan time of the image display device.

2. Ultrasonic imaging apparatus according to claim 1, characterized by the control means being operable to control said auxiliary memory (29) in such manner that currently developing lines of an ultrasonic echo image are written line-by-line into the auxiliary memory (29)

simultaneously with their relaying via said real time signal path to the sequentially operating memories (17, 18) and to the image display device (9).

3. Ultrasonic imaging apparatus according to claim 1, characterized by the auxiliary memory (29) being controlled in such manner that lines stored in the auxiliary memory (29) are read out via the sequentially operating memories (17, 18) for recording on the image display device (9) selectively without and together with further current lines of a direct scanning supplied via said real time signal path.

4. Ultrasonic imaging apparatus according to claim 1, characterized in that said control means comprises a basic cycle generator (25) operating at a basic pulse rate ($T_G$), the control of the auxiliary memory (29) for the specification of the read-in or, respectively, read-out times being in turn controlled by the basic pulse ($T_G$) of said basic cycle generator (25).

5. Ultrasonic imaging apparatus according to claim 9, characterized in mixer means having first mixer input means forming part of said real time signal path and second mixer input means connected with said echo line auxiliary memory, and having mixer output means connected with said frequency converter memories, first input switch means controlling transmission of a current line sequence of echo impulses via said real time signal path including said first mixer input means to said frequency converter memories, and second input switch means for controlling transmission of a previously stored line sequence from said further memory to said frequency converter memories via said second mixer input means, said first and second input switch means being selectively concurrently and individually operable to connect the mixer stage (31):
  (a) only with the current line sequences of echo impulses from said real time signal path;
  (b) only with previously stored line sequences from the echo line auxiliary memory; and
  (c) with both said current line sequences from said real time signal path, and said previously stored line sequences from said echo line auxiliary memory.

6. Ultrasonic imaging apparatus according to claim 5, further characterized in a first buffer memory (34) forming part of said real time signal path and being connected in series with the first mixer input means such that the current line sequence of echo impulses is supplied to the mixer means via the first buffer memory, and a second buffer memory (32) being connected in series between said echo line auxiliary memory and said second mixer input means such that the previously stored line sequence from the echo line auxiliary memory is supplied to the mixer means via the second buffer memory.

7. Ultrasonic imaging apparatus according to claim 5, further characterized in said first and second input switch means (33, 35) being manually controlled key switches.

8. Ultrasonic imaging apparatus according to claim 5, further characterized in said first and second input switch means (33, 35) being automatically operable.

9. Ultrasonic imaging apparatus according to claim 5, with said auxiliary memory (29) being operable to alter the scale of the line sequences supplied thereby in comparison with the current line sequence as supplied by said ultrasonic applicator.

* * * * *